(12) United States Patent
Shin et al.

(10) Patent No.: US 10,376,453 B1
(45) Date of Patent: Aug. 13, 2019

(54) COMPOSITION FOR PROMOTING HAIR GROWTH CONTAINING NOVEL PANTETHEINE DERIVATIVE

(71) Applicant: KOREA INSTITUTE OF OCEAN SCIENCE AND TECHNOLOGY, Gyeonggi-do (KR)

(72) Inventors: Hee Jae Shin, Gyeonggi-do (KR); Min Ah Lee, Gyeonggi-do (KR); Mojid Mondol, Gyeonggi-do (KR); Hyi-Seung Lee, Seoul (KR); Jong Seok Lee, Gyeonggi-do (KR); Yeon-Ju Lee, Gyeonggi-do (KR)

(73) Assignee: KOREA INSTITUTE OF OCEAN SCIENCE AND TECHNOLOGY, Gyeonggi-Do (KR)

( * ) Notice: Subject to any disclaimer, the term of this patent is extended or adjusted under 35 U.S.C. 154(b) by 0 days.

(21) Appl. No.: 16/415,248

(22) Filed: May 17, 2019

Related U.S. Application Data

(63) Continuation of application No. 15/394,153, filed on Dec. 29, 2016.

(51) Int. Cl.
  *A61K 8/46* (2006.01)
  *A61Q 7/00* (2006.01)

(52) U.S. Cl.
  CPC . *A61K 8/46* (2013.01); *A61Q 7/00* (2013.01)

(58) Field of Classification Search
  CPC .................................. A61K 8/46; A61Q 7/00
  See application file for complete search history.

(56) References Cited

FOREIGN PATENT DOCUMENTS

| KR | 1019850002397 | 5/1985 | |
|---|---|---|---|
| KR | 1020060048090 | 5/2006 | |
| KR | 1008397040000 | 6/2008 | |
| KR | 1020120039384 | 4/2012 | |
| WO | WO9511673 | 5/1995 | |
| WO | WO-9511673 A1 * | 5/1995 | ............. A61K 31/16 |

OTHER PUBLICATIONS

Zavod, R.M. et al. "Drug design and relationship of functional groups to pharmacological activity" D.A. Williams, T.L. Lemke (Eds.), Faye's Principles of Medicinal Chemistry, Lippincott Williams Wilkins, Baltimore (2002), pp. 37-67 (Year: 2002).

* cited by examiner

*Primary Examiner* — Andrew S Rosenthal
(74) *Attorney, Agent, or Firm* — IPLA P.A.; James E. Bame

(57) ABSTRACT

Provided is a composition for promoting hair growth, containing, as an active ingredient, a new compound represented by the following formula 1 or a salt thereof, which exhibits an excellent effect of promoting the growth of dermal papilla cells to thereby exhibit the effect of promoting hair growth: Formula 1

Formula 1

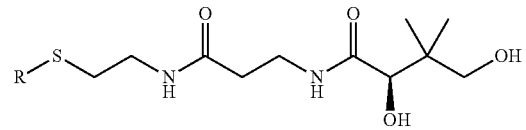

wherein R is any one selected from the group consisting of 4-pentenoyl, 10-undecenoyl, isobutyl formate, and 2,4-dihydroxybenzoyl.

8 Claims, 2 Drawing Sheets

COMPOSITION FOR PROMOTING HAIR GROWTH CONTAINING NOVEL PANTETHEINE DERIVATIVE

CROSS REFERENCE

This is a continuation of application Ser. No. 15/394,153 which is now pending, whose entire contents are incorporated herein by reference.

BACKGROUND

1. Technical Field

The present invention relates to a composition for promoting hair growth, and more particularly to a composition for promoting hair growth, which contains a new pantetheine derivative that exhibits an excellent effect of promoting the growth of dermal papilla cells to thereby promote hair growth.

2. Description of the Related Art

The known causes of hair loss include excessive male hormone production, excessive sebum secretion, scalp function deterioration caused by peroxides, bacteria, etc., genetic factors, aging, stress, and the like. In addition, the hair loss population is gradually increasing due to increased social stress, environmental pollution, westernized eating habits such as the consumption of instant foods, frequent permanent waves and hair color changes, etc.

The hair cycle can be divided into four separate stages: anagen where hair grows; catagen where hair growth stops and the hair bulb shrinks; telogen where the dermal papilla stops its activity and hair remains on the scalp; and exogen where the dermal papilla initiates its activity or produces new hair to shed old hair.

The anagen stage (2-7 years) is a stage where hair grows. It is subdivided into two stages: a hair production stage where hair extends from the hair bulb to the hair follicle; and a stage where hard keratin is produced in the hair follicle. Hair continues to grow until the catagen stage.

The catagen stage (2-3 weeks) following the anagen stage is a stage where the metabolism of hair becomes slower while the shape of hair is maintained. In this step, keratin is not produced. The hair in the catagen stage occupies 1% of the total number of hairs. In this stage, the hair bulb shrinks to be divided into hair papillae, which are surrounded by hair follicles and move upward, and cell division is arrested.

The telogen stage (3 months) is a stage where the hair papilla and the hair follicle gradually contracts and where the hair root is pushed upward and falls out. This stage where hair falls out continues for 3-4 months until the next anagen stage is started.

Normal persons have a relatively large number of anagen-stage hairs, whereas persons with alopecia have a relatively large number of telogen-stage hairs, and thus have visible hair loss. As hair loss progresses, the period of the anagen stage becomes shorter, and for this reason, hair gradually becomes thinner. Therefore, for the treatment of hair loss, it is important to facilitate telogen-stage hair follicles to enter the anagen stage and to extend the shortened anagen stage.

Male pattern alopecia (androgenetic alopecia) is caused by the male hormone testosterone. If testosterone is converted to the highly active hormone dihydrotestosterone (DHT) by the enzyme 5α-reductase, the hormone dihydrotestosterone will act on hair follicles to induce anagen-stage hair follicles to enter the catagen stage, thereby causing hair loss. For this reason, for the treatment of androgenetic alopecia, methods for inhibiting DHT production caused by 5α-reductase have been mainly used.

Female pattern alopecia is caused mainly by a decrease in estrogen level after the menopause. As a therapeutic agent against female pattern alopecia, minoxidil or estrogen has been mainly used.

Alopecia areata is caused by autoimmune diseases, mental stress, or genetic factors. The causes of alopecia areata fundamentally differ from those of androgenetic alopecia, and a method for treating alopecia areata also differs from a method for treating androgenetic alopecia. Thus, for the treatment of alopecia areata, a method of applying minoxidil to a hair loss area or artificial stimulation in a hair loss area has been used.

However, agents such as minoxidil or trichosaccharides, known to date to have effects on hair loss prevention and hair growth promotion, have no distinct effect and cause side-effects such as induction of skin irritation. Thus, there is an urgent need to develop compositions having demonstrated safety and desired effects.

SUMMARY OF THE INVENTION

An object of the present invention is to provide a hair growth stimulant, which is capable of promoting the proliferation of dermal papilla cells to thereby prevent, alleviate or treat hair loss and exhibit excellent effects on hair growth or the like, and a cosmetic or pharmaceutical composition for promoting hair growth, which contains the hair growth stimulant.

To accomplish the above object, the present invention provides a composition for promoting hair growth, containing, as an active ingredient, a compound represented by the following formula 1 or a salt thereof:

Formula 1

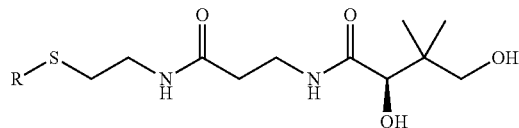

wherein R is any one selected from the group consisting of 4-pentenoyl, 10-undecenoyl, isobutyl formate, and 2,4-dihydroxybenzoyl.

In the composition for promoting hair growth according to the present invention, the compound represented by formula 1 is preferably any one selected from the group consisting of 4-pentenoyl-D-pantetheine, 10-undecenoyl-D-pantetheine, isobutyl formate-D-pantetheine, and 2,4-dihydroxybenzoyl-D-pantetheine.

In the composition for promoting hair growth according to the present invention, the compound represented by formula 1 exhibits the effect of promoting the growth of dermal papilla cells.

In the composition for promoting hair growth according to the present invention, the compound represented by formula 1 may be prepared using D-pantethine as a starting material.

The composition for promoting hair growth according to the present invention may be a cosmetic composition for preventing hair loss and promoting hair growth.

In the composition for promoting hair growth according to the present invention, the cosmetic composition preferably has any one formation selected from the group consisting of hair tonics, hair conditioners, hair essence, hair lotion, hair nourishing lotion, hair shampoo, hair rinse, hair treatments, hair cream, hair nourishing cream, hair moisturizer cream, hair massage cream, hair wax, hair aerosols, hair packs, hair nourishing pack, hair soap, hair cleansing foam, hair oil, hair drying preparations, hair preservation treatments, hair colorants, hair weaving preparations, color-removing preparations for hair, hair gel, hair glazes, hair dressingers, hair lacquers, hair moisturizers, hair mousse, and hair sprays.

The composition for promoting hair growth according to the present invention may be a pharmaceutical composition for preventing hair loss and promoting hair growth.

In the composition for promoting hair growth according to the present invention, the pharmaceutical composition preferably has any one formation selected from the group consisting of ointments, pastes, gels, jellies, serums, aerosol sprays, non-aerosol sprays, foams, creams, lotions, solutions, and suspensions.

The hair growth stimulant according to the present invention exhibits the effect of promoting the proliferation of human dermal papilla cells to thereby prevent hair loss and promote hair growth. Thus, the hair growth stimulant may be effectively used as an active ingredient in cosmetic or pharmaceutical compositions for preventing hair loss and promoting hair growth.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Figure 1:
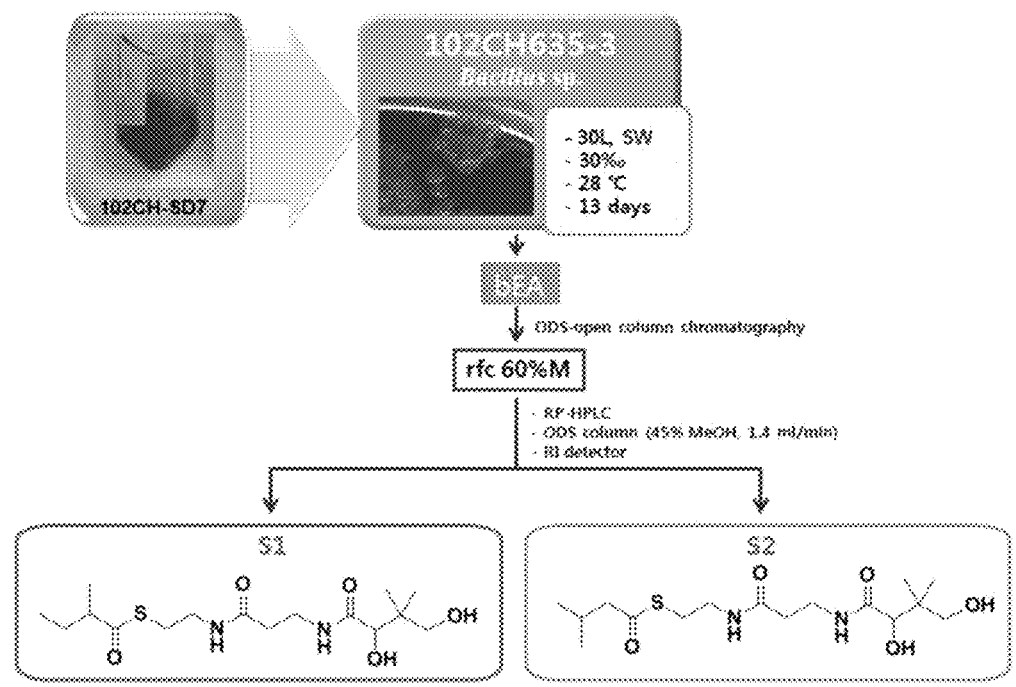
FIG. 1 shows a process of isolating new compounds (S1 and S2) for hair loss prevention and hair growth promotion from a culture broth of a 102CH635-3 strain.

Hereinafter, the present invention will be described in detail.

The development and growth of hair and the hair cycle are controlled by hair papilla which is a tissue derived from the mesoderm of the hair follicle base. It is known that the hair papilla interacts with hair matrix cells and stimulates these cells to differentiate into several types of cells that form hair follicles and hairs.

Hair follicles undergo repeated hair cycles, each consisting of anagen phase-catagen phase-telogen phase, and hair grows and falls out during each cell cycle. This cell cycle process is controlled by the interactions between mesodermal and ectodermal cells, and dermal papilla cells play a key role in this control. Mesodermal (dermal papilla) cells induce the production of hair in the anagen phase, and then secrete a substance that stimulates the growth of hair. The catagen phase begins in response to a change in dermal papilla cells, and as hair follicles degenerate, hair papilla moves upward and is placed immediately below the hair bulge in which hair stem cells exist. Following the telogen phase, the anagen phase begins in which hair stem cells divide by the signal of dermal papilla cells to form new hair follicles.

According to the literature, the size and volume of dermal papillae in alopecia patients are significantly smaller than those in normal persons. The number of dermal papillae increases in the anagen phase of the hair cycle, and the volume thereof is dependent on the number of cells forming these dermal papillae. Furthermore, the volume and division of the epithelial tissue of the hair bulb are also dependent on the volume of dermal papillae.

When a new anagen phase begins following the telogen stage, signals similar to those in the exogen stage act. It was reported that, in the initial stage of the anagen stage, the signal of Wnt protein in the epithelial cells of the hair bulge adjacent to dermal papilla cells is very strong, and Wnt/β-catenin signals or the like play an important role.

It is reported that the Wnt/β-catenin signaling system promotes the formation of hair follicles ("WNT signals are required for the initiation of hair follicle development." Andl T, et al. (2002) Dev Cell. 2: 643-653), and plays an important role in maintaining and activating genes that are expressed during the anagen stage of the hair cycle ("Wnt signaling maintains the hair-inducing activity of the dermal papilla." Kishimoto J, et al. (2000) Genes Dev 14: 1181-1185), and promote differentiation from stem cells to keratinocytes ("β-catenin controls hair follicle morphogenesis and stem cell differentiation in the skin." Huelsken J, et al. (2001) Cell 105: 533-545).

The present inventors have found that a composition containing, as an active ingredient, a compound represented by the following formula 1 or a salt thereof, promotes the proliferation of dermal papilla cells to thereby increase the gene expression level of dermal papilla cells related to hair loss prevention or hair growth promotion, thereby completing the present invention:

Formula 1

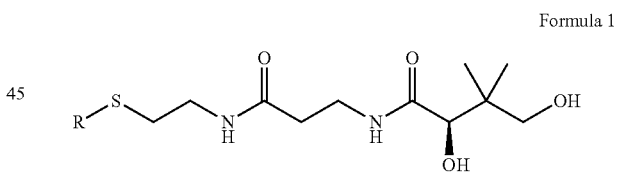

wherein R is any one selected from the group consisting of 2-methylbutyryl, 3-methylbutyryl, cinnamoyl, 4-pentenoyl, 10-undecenoyl, isobutyl formate, 2,4-dihydroxybenzoyl, geranyl, farnesyl, acryloyl, propanone, 2-pentanone, 1-(4-hydroxyphenyl)ethanone, 1-(2,4-dihydroxyphenyl)ethanone, pentanoic acid, 2-hydroxypropanoic acid, 2-phenylacetic acid, 2-(4-(propanoyl)phenyl)acetic acid, 4-methylbenzoic acid, 4-(4-phenyl)-4-oxobutanoic acid, 2-oxoethyl acetyl, 2-phenoxyacetyl, 2-(benzyloxy)acetyl, 4-methoxybenzoyl, 3,5-dimethylphenol, 6-methoxybenzene-1,4-diol, propenylbenzene, and 4-hydroxycoumarin.

Preferably, the compound represented by formula 1 is any one selected from the group consisting of 2-methylbutyryl-D-pantetheine, 3-methylbutyryl-D-pantetheine, cinnamoyl-D-pantetheine, 4-pentenoyl-D-pantetheine, 10-undecenoyl-D-pantetheine, isobutyl formate-D-pantetheine, 2,4-dihydroxybenzoyl-D-pantetheine, and geranyl-D-pantetheine.

It is to be understood that the compound of formula 1, which is used in the present invention, may be provided not only as a free compound, but also as a pharmaceutically acceptable salt thereof, a pharmaceutically acceptable solvate thereof, a pharmaceutically acceptable polymorph thereof, or a pharmaceutically acceptable prodrug thereof. In addition, the active ingredient may be used alone or in combination with one or more other pharmacologically active compounds.

A salt of the compound of formula 1, which is used as an active ingredient in the composition for promoting hair growth is not specifically limited, as long as it may be used in medical or cosmetic preparations. The salt may include an inorganic salt or an organic salt, and may be an acidic salt or an alkaline salt.

The composition according to the present invention may further contain one or more other drugs or additives for the prevention or treatment of hair loss or the promotion of hair growth. The other drugs or additives include, but are not limited to, retinoic acid, minoxidil, finasteride, zinc peptides, zinc oxide, biotin, genistein, onion extracts, pumpkin seed oil, Emu oil, green tea extracts, Willow bark extracts, and the like.

The composition for promoting hair growth according to the present invention may contain, based on the total amount of the composition, about 0.01-25 wt % of the compound of formula 1, and the content of the compound of formula 1 in the composition may vary depending on the kind of compound of formula 1.

Where the composition for promoting hair growth according to the present invention is used as a pharmaceutical composition, may be applied topically to a portion in need of the prevention or treatment of hair loss or the promotion of hair growth, once or twice a day. When the content of the active ingredient in the composition is 1 wt %, the amount applied per day may be about 0.5-3 mg/cm$^2$ (skin surface area), and may vary depending on the area of a portion to which the active ingredient is to be applied. The amount and frequency of this application may be suitably determined depending on the patient's age and sex and the severity of hair loss.

A pharmaceutical composition containing the compound of formula 1 or a salt thereof may further contain a suitable carrier, excipient and/or diluent, which is generally used in the preparation of pharmaceutical compositions.

The active ingredient of the composition of the present invention may be formulated with excipients, such as fillers, extenders, binders, wetting agents, disintegrants, surfactants or the like, or diluents, which are commonly used. The composition of the present invention may further comprise an anti-coagulant, a lubricant, fragrance, an emulsifier, a preservative or the like, and may be formulated using a method well known in the art so as to provide quick, sustained or delayed release of the active ingredient after administration to mammals.

The pharmaceutical composition according to the present invention may be prepared as a conventional pharmaceutical formulation known in the field to which the present invention pertains. Preferably, it may be prepared as a formulation for transdermal administration or a skin external preparation for topical application.

Specifically, the composition of the present invention may be prepared as any formulations for skin application, for example, ointments, pastes, gels, jellies, serums, aerosol sprays, non-aerosol sprays, foams, creams, lotions, solutions, or suspensions.

A functional cosmetic composition containing, as an active ingredient, the hair growth stimulant of the present invention, may be prepared as any formulation for skin application. More specifically, the functional cosmetic composition may be prepared as a formulation selected from among hair tonic, hair conditioner, hair essence, hair lotion, hair nourishing lotion, hair shampoo, hair rinse, hair treatment, hair cream, hair nourishing cream, hair moisturizer cream, hair massage cream, hair wax, hair aerosol, hair pack, hair nourishing pack, hair soap, hair cleansing foam, hair oil, hair drying preparations, hair preservation treatments, hair colorants, hair weaving preparations, color-removing preparations for hair, hair gel, hair glazes, hair dressingers, hair lacquers, hair moisturizers, hair mousse, and hair sprays. In addition, it may be formulated in the form of skin contact materials such as cosmetic products, detergents or fibers.

In a cosmetic composition having each formulation according to the present invention, components other than the component of formula 1 or a salt thereof may be suitably selected and added by a person skilled in the art within a range that does not impair the purpose and effect of the present invention. Examples of components that may be added to the cosmetic composition of the present invention include oil and fat components, skin moisturizers, emollient agents, surfactants, organic or inorganic pigments, organic powder, UV-absorbing agents, preservatives, sterilizers, antioxidants, plant extracts, pH adjusting agents, alcohols, pigments, fragrance, blood circulation promoters, antiperspirants purified water, and the like.

Hereinafter, the present invention will be described in further detail with reference to examples. However, it will be obvious to those skilled in the art that these examples are for illustrative purposes only and various changes and modifications are possible departing from the scope and technical spirit of the present invention as disclosed in the appended claims.

1. Isolation and Identification of *Bacillus* sp. 102CH635-3 Strain

Microorganisms were isolated from marine sediment collected from the vicinity of the Chuuk Lagoon, Micronesia, in February 2010. 1 g of the marine sediment was heat-treated at 60° C. for 20 minutes, and then streaked on a BN agar plate. The microorganisms were cultured at 28° C. for 7 days while being observed, and an orange single colony of a 102CH635-3 strain growing while spreading flatly was isolated. The 102CH635-3 strain was preserved in 40% glycerol at −70° C.

For 16S rRNA sequencing of 102CH635-3, genomic DNA was amplified by PCR using 16S rRNA primers (27F 5'(AGA GTT TGA TCM TGG CTC AG)3' and 1492R 5'(TAC GGY TAC CTT GTT ACG ACT T)3'). Specifically, a mixture of 20 ng of genomic DNA and 30 μl of EF-Taq (SolGent, Korea) reaction solution was subjected to PCR for 35 cycles. The PCR reaction was performed under the following conditions: 35 cycles, each consisting of denaturation at 95° C. for 1 min, primer annealing at 55° C. for 1 min, and chain extension at 72° C. for 1 min; followed by final chain extension at 72° C. for 10 minutes. A nucleotide sequence having a length of 1,380 bp or more was obtained from the amplified DNA, and analyzed using an ABI prism 3730XL DNA analyzer (Applied Biosystems, Foster City, Calif.). The homology of the nucleotide sequence of the obtained marine microorganisms to those of strains deposited in the NCBI was analyzed by Blast search. As a result, the 102CH635-3 strain showed a sequence homology of 99% to *Bacillus subtilis* and a sequence homology of 99% to *Bacillus amyloliquefaciens*, and thus it was identified to be *Bacillus* sp.

2. Establishment of Culture Conditions

A single colony of *Bacillus* sp. 102CH635-3 was inoculated into a flask containing 50 ml of BN broth and was cultured at 28° C. for 7 days. The culture broth was extracted with ethyl acetate and concentrated under reduced pressure to obtain a crude extract. The analysis of $^1$H NMR data for the crude extract indicated that the strain produced an interesting substance. Thus, the strain was selected as a useful strain for isolation of an active compound. Prior to mass culture of the strain, an experiment for establishing optimal culture conditions under which an active compound is produced was performed. As shown in Table 1 below, the BN medium from which the strain was isolated, and an SWNB medium prepared by adding sea salt to an NB medium that is generally used for *Bacillus* sp., were used.

TABLE 1

| Composition of the culture media | | |
|---|---|---|
| | BN | SWNB |
| Components | g/L | |
| D-glucose | 10 | — |
| Tryptone | 2 | — |
| Peptone | — | 5 |
| Yeast extract | 1 | — |
| Beef extract | 1 | 3 |
| Glucose | 5 | — |
| Temperature (° C.) | 28 | 28 |
| Shaking speed (rpm) | 140 | 140 |
| Sea salt | 32 | 32 |
| pH | 7.0 | 7.0 |
| Culture duration (days) | 7 | 7 |

The 102CH635-3 strain was inoculated into 200 mL of each of broths having different medium compositions, after which it was cultured at 28° C. for 7 days, and then extracted with ethyl acetate and concentrated under reduced pressure, thereby obtaining crude extracts. The $^1$H NMR data of the culture crude extracts obtained using the different medium compositions were analyzed. As a result, it could be seen that the use of the SWNB medium was effective for production of a useful compound. Thus, the SWNB medium was used as an optimal culture medium for mass culture.

3. Mass Culture, and Isolation and Structural Determination of New Compounds (S1 and S2) for Hair Loss Prevention/Hair Growth Promotion A single colony of the *Bacillus* sp. 102CH635-3 strain was inoculated and seed-cultured at 28° C. and 120 rpm for 7 days. For mass culture, the seed strain was inoculated into a large-scale fermenter containing 30 liters of SWNB medium and was cultured at 28° C. for 13 days. 30 liters of the resulting culture broth was centrifuged by a continuous centrifuge, and the culture filtrate was extracted twice with the same amount of ethyl acetate, and the mycelium was extracted twice with methanol. The extract was concentrated by a vacuum evaporator to obtain a crude extract which was then stored at −20° C. until use as a sample for isolation.

The ethyl acetate extract of the culture filtrate was fractionated by reverse-phase chromatography. As an elution solvent, a water/methanol mixture was used, and the ethyl acetate extract was fractionated into 5 fractions (from a 20% methanol fraction to a 100% methanol fraction). The 60% methanol fraction was concentrated under reduced pressure, dried, and then recovered. This fraction was purified by C18 reversed-phase HPLC (column: YMC-ODS-A, 5 μm, 10×250 mm; solvent: 45% MeOH; elution rate: 1.5 ml/min; RI detector) to isolate two single compounds. The finally isolated new compounds were 2-methylbutyryl-D-pantetheine (S1; 0.5 mg) and 3-methylbutyryl-D-pantetheine (S2; 1.9 mg) (see FIG. 1).

Structural elucidation by analysis of spectrometric data such as 1D NMR, 2D NMR and HR-ESIMS indicated that S1 and S2 are new pantetheine derivatives. S1 showed a peak at m/z 385.1778 [M+Na]$^+$ in HR-ESIMS and was determined to have a molecular formula of $C_{16}H_{30}N_2O_5S$. The $^1$H NMR spectrum of S1 showed that S1 has 4 methyl groups and 6 methylene groups. The COSY spectrum of S1 showed the couplings of four methylene groups, H-5/H-6 and H-8/H-9, and the HMBC spectrum revealed a partial structure of S1 by showing the correlations between the amide carbons, C-4 (δ 176.2) and C-7 (δ 174.0), and the neighboring hydrogen atoms. In addition, comparison with that reported in the literature indicated that S1 has a partial structure of pantetheine. Furthermore, the HMBC spectrum of S1 showed HMBC correlations between the carbonyl carbon at C-10 (δ 205.0) and H-9 (δ 3.00), H-12 (δ 1.48, 1.71) and H-14 (δ 1.15), indicating that S1 is a new compound having a structure in which a 2-methylbutyl group is attached to pantetheine. Moreover, in order to determine the stereochemistry of C-3, the $[\alpha]_D$ value of S1 was compared with that of D-pantetheine reported in the literature, and as a result, it was determined that S1 and D-pantetheine have similar $[\alpha]_D$ values of +12.2 (c 3.45, $H_2O$) and +23.7 (c 0.5, $H_2O$), respectively. Thus, S1 was determined to be 2-methylbutyryl-D-pantetheine. The HR-ESIMS of S2 showed that S2 has a molecular formula of $C_{16}H_{30}N_2O_5S$, suggesting that S2 has the same molecular weight and molecular formula as those of S1. Analysis of various 1D and 2D NMR data, including $^1$H NMR, $^{13}$C NMR and HMBC data, indicated that S2 has a structure very similar to that of S1. However, the COSY and HMBC spectra indicated that S2 has a partial structure of a 3-methylbutyl group in which the methyl group at δ 0.95 (d, J=5.0) is attached to a position different from that in S1. Thus, the structure of S2 was determined to be 3-methylbutyryl-D-pantetheine. In addition, the results of database search indicated that S2 is a new compound that has not yet been reported.

S1: $[\alpha]_D$+23.7 (c 0.5, $H_2O$), $^1$H NMR (CD$_3$OD, 500 MHz) 0.92 (s, CH$_3$), 0.92 (s, CH$_3$), 0.92 (t, CH$_3$), 1.15 (d, J=5.0, CH$_3$), 1.48-1.71 (m, CH$_2$), 2.41 (t, CH$_2$), 2.59 (m, CH), 3.00 (t, CH$_2$), 3.32 (t, CH$_2$), 3.38-3.46 (d, J=10.0, CH$_2$), 3.47 (m, CH$_2$), 3.89 (s, CH), $^{13}$C NMR (CD$_3$OD, 125 MHz) 12.1, 17.8, 21.1, 21.5, 28.4, 29.0, 36.5, 36.6, 40.3, 40.5, 51.5, 70.5, 77.4, 174.0, 176.2, 205.0, HR-ESIMS m/z 385.1778 [M+Na]+(calculated for $C_{16}H_{30}N_2O_5NaS$, 385.1773).

S2: $[\alpha]_D$+7.7 (c 0.5, $H_2O$), $^1$H NMR (CD$_3$OD, 500 MHz) 0.92 (s, CH$_3$), 0.92 (s, CH$_3$), 0.95 (d, J=5.0, CH$_3$), 0.95 (d, J=5.0, CH$_3$), 2.13 (m, CH), 2.41 (t, CH$_2$), 2.46 (d, J=5.0, CH$_2$), 3.00 (t, CH$_2$), 3.32 (t, CH$_2$), 3.38-3.46 (d, J=10.0, CH$_2$), 3.47 (m, CH$_2$), 3.89 (s, CH), $^{13}$C NMR (CD$_3$OD, 125 MHz) 21.1, 21.5, 22.7, 22.7, 27.8, 29.3, 36.5, 36.6, 40.3, 40.5, 53.8, 70.5, 77.4, 174.0, 176.2, 200.2, HR-ESIMS m/z 385.1779 [M+Na]$^+$ (calculated for $C_{16}H_{30}N_2O_5NaS$, 385.1773).

TABLE 2

NMR data for S1 and S2 in CD₃OD

| No | S1 $\delta_c$ | S1 $\delta_H$, mult. (J in Hz) | S1 HMBC | S2 $\delta_c$ | S2 $\delta_H$, mult. (J in Hz) | S2 HMBC |
|---|---|---|---|---|---|---|
| 1 | 70.5 | 3.38, 3.46 d (J = 10.0) | C2, C3 | 70.5 | 3.38, 3.46 d (J = 10.0) | C3 |
| 2 | 40.5 | | | 40.5 | | |
| 3 | 77.4 | 3.89, s | C2, C4, C15 | 77.4 | 3.89, s | C4 |
| 4 | 176.2 | | | 176.2 | | |
| 5 | 36.5 | 3.47, m | C4, C6, C7 | 36.5 | 3.47, m | C4, C6, C7 |
| 6 | 36.6 | 2.41, t | C5, C7 | 36.6 | 2.41, t | C5, C7 |
| 7 | 174.0 | | | 174.0 | | |
| 8 | 40.3 | 3.32, t | C7, C8 | 40.3 | 3.32, t | C7, C9 |
| 9 | 29.0 | 3.00, t | C8, C10 | 29.3 | 3.00, t | C8, C10 |
| 10 | 205.0 | | | 200.2 | | |
| 11 | 51.5 | 2.59, m | C12 | 53.8 | 2.46, d (J = 5.0) | C10, C12, C14 |
| 12 | 28.4 | 1.48, 1.71, m | C10, C11 | 27.8 | 2.13, m | |
| 13 | 12.1 | 0.92, t | C11, C12 | 22.7 | 0.95, d (J = 5.0) | C11, C12, C14 |
| 14 | 17.8 | 1.15, d (J = 5.0) | C10, C11, C12 | 22.7 | 0.95, d (J = 5.0) | C11, C12, C13 |
| 15 | 21.1 | 0.92, s | C3, C2, C16 | 21.1 | 0.92, s | C2, C3, C16 |
| 16 | 21.5 | 0.92, s | C1, C15 | 21.5 | 0.92, s | C1, C2, C15 |

4. Synthesis of the New D-Pantetheine Compounds (S1 and S2) and their Derivatives It is known that pantethine and pantetheine are the components of CoA (coenzyme A) and ACP (acyl carrier protein) and are involved in fatty acid and carbohydrate metabolisms after hydrolysis. It was reported that these compounds play a role in metabolic reactions, including fatty acid oxidation, amino acid degradation and cholesterol synthesis, and have effects against hyperlipidemia, hematological diseases, renal diseases, arteriolosclerosis, diabetes, and the like. Calcium-D-pantetheine-S-sulfonate is known to have whitening activity, moisturizing activity, melanin production inhibitory activity and anti-aging activity such as skin inflammation inhibitory activity, and thus has been used as an additive in famous cosmetic products in Korea and other countries. Thus, in order to synthesize the new D-pantetheine compounds isolated from the 102CH635-3 strain and their derivatives, studies on the synthesis of D-pantetheine compounds were conducted using D-pantethine, thereby synthesizing not only the new natural compounds (S1 and S2), but also their derivatives.

Figure 2:
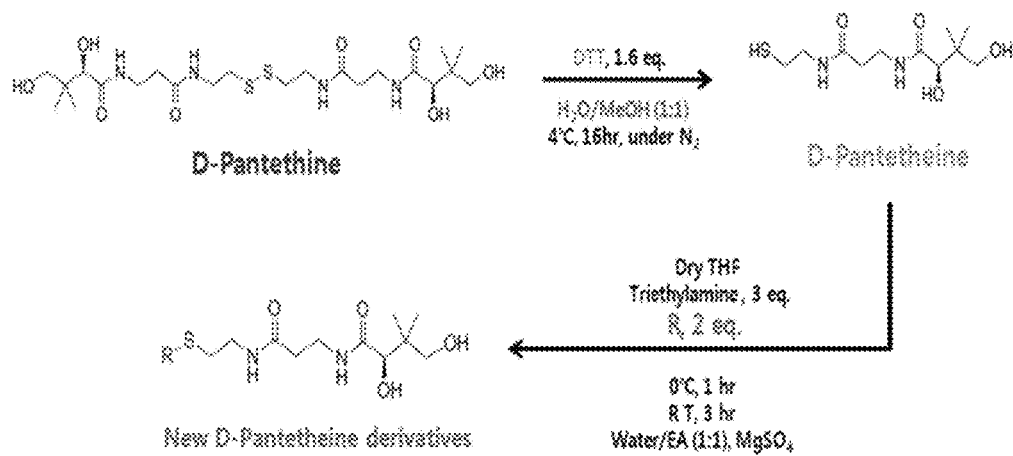
FIG. 2 shows a method of synthesizing new D-pantetheine derivatives according to the present invention.

Using commercially available D-pantethine (P2125, SIGMA), various new derivatives of D-pantetheine were synthesized according to the method shown in FIG. 2. In a detailed synthetic method, dithiothreitol (DTT) and H₂O:MeOH (1:1, v/v) were added to D-pantethine, and the mixture was allowed to react at 4° C. for 16 hours under N₂ atmosphere. After it was confirmed by TLC that D-pantethine disappeared, the reaction was terminated, and the solvent was removed. Dry tetrahydrofuran (THF) and triethylamine were added to the reaction product (pantetheine) from which the solvent has been removed, and each of reagents having various functional groups (R) was added thereto, after each of the mixtures was allowed to react at 0° C. for 2 hours and at room temperature for 3 hours.

Herein, R is one of 2-methylbutyryl, 3-methylbutyryl, cinnamoyl, 4-pentenoyl, 10-undecenoyl, isobutyl formate, 2,4-dihydroxybenzoyl, geranyl, farnesyl, acryloyl, propanone, 2-pentanone, 1-(4-hydroxyphenyl)ethanone, 1-(2,4-dihydroxyphenyl)ethanone, 1-(2,4-dihydroxyphenyl)ethanone, pentanoic acid, 2-hydroxypropanoic acid, 2-phenylacetic acid, 2-(4-(propanoyl)phenyl)acetic acid, 4-methylbenzoic acid, 4-(4-phenyl)-4-oxobutanoic acid, 2-oxoethyl acetyl, 2-phenoxyacetyl, 2-(benzyloxy)acetyl, 4-methoxybenzoyl, 3,5-dimethylphenol, 6-methoxybenzene-1,4-diol, propenylbenzene, and 4-hydroxycoumarin.

After the reaction solvent was completely removed, the remaining material was solvent-fractionated with H₂O:ethyl acetate (EtOAC) (1:1, v/v), and the ethyl acetate layer was recovered, treated with MgSO₄, and then concentrated to obtain reaction products. It was confirmed by LR-APCIMS that the desired compounds were synthesized, and the products were separated using HPLC. Purification was performed using C18 reversed-phase HPLC (column: YMC-ODS-A, 5 μm, 10×250 mm; solvent: 60% MeOH; elution rate: 1.5 mL/min; RI detector) to separate various new derivatives.

Among the synthesized new derivatives, 2-methylbutyryl-D-pantetheine, 3-methylbutyryl-D-pantetheine, cinnamoyl-D-pantetheine, 4-pentenoyl-D-pantetheine, 10-undecenoyl-D-pantetheine, isobutyl formate-D-pantetheine, 2,4-dihydroxybenzoyl-D-pantetheine and geranyl-D-pantetheine were analyzed by $^1$H NMR, $^{13}$C NMR and MS spectrometry to determine their structures. It is to be understood that new derivatives not described in this example can also be synthesized according to the proposed synthetic method.

S1 (2-methylbutyryl-D-pantetheine): $[\alpha]_D$+9.9 (c 1.0, H₂O), $^1$H NMR (CD₃OD, 500 MHz) 0.92 (s, CH₃), 0.92 (s, CH₃), 0.92 (t, CH₃), 1.15 (d, J=5.0, CH₃), 1.48-1.71 (m, CH₂), 2.41 (t, CH₂), 2.59 (m, CH), 3.00 (t, CH₂), 3.32 (t, CH₂), 3.38-3.46 (d, J=10.0, CH₂), 3.47 (m, CH₂), 3.89 (s, CH), $^{13}$C NMR (CD₃OD, 125 MHz) 12.1, 17.8, 21.1, 21.5, 28.4, 29.0, 36.5, 36.6, 40.3, 40.5, 51.5, 70.5, 77.4, 174.0, 176.2, 205.0, LR-APCIMS m/z 360.99 [M−H]⁻, 362.87 [M+H]⁺, C₁₆H₃₀N₂O₅S.

S2 (3-methylbutyryl-D-pantetheine): $[\alpha]_D$+5.9 (c 1.0, H₂O), $^1$H NMR (CD₃OD, 500 MHz) 0.92 (s, CH₃), 0.92 (s, CH₃), 0.95 (d, J=5.0, CH₃), 0.95 (d, J=5.0, CH₃), 2.13 (m, CH), 2.41 (t, CH₂), 2.46 (d, J=5.0, CH₂), 3.00 (t, CH₂), 3.32 (t, CH₂), 3.38-3.46 (d, J=10.0, CH₂), 3.47 (m, CH₂), 3.89 (s, CH), $^{13}$C NMR (CD₃OD, 125 MHz) 21.1, 21.5, 22.7, 22.7, 27.8, 29.3, 36.5, 36.6, 40.3, 40.5, 53.8, 70.5, 77.4, 174.0, 176.2, 200.2, LR-APCIMS m/z 363.14 [M+H]⁺, C₁₆H₃₀N₂O₅S.

S3 (cinnamoyl-D-pantetheine): $^1$H NMR (CD₃OD, 500 MHz) 0.92 (s), 2.42 (t), 3.15 (t), 3.35-3.51 (m), 3.89 (s), 6.86 (d, J=15.0), 7.41-7.42 (m), 7.62-7.66 (m), $^{13}$C NMR (CD₃OD, 125 MHz) 21.1, 21.5, 29.4, 36.5, 36.6, 40.3, 40.5, 50.0, 70.5, 77.4, 125.9, 129.8, 130.3, 132.0, 135.6, 142.3, 176.2, 191.2, LR-APCIMS m/z 408.15 [M−H]⁻, 409.02 [M+H]⁺, C₂₀H₂₈N₂O₅S.

S4 (4-pentenoyl-D-pantetheine): $^1$H NMR (CD₃OD, 500 MHz) 0.92 (s), 2.36-2.42 (m), 2.68 (t), 3.01 (t), 3.32 (t), 3.33-3.53 (m), 3.89 (s), 4.98 (d, J=10.0), 5.05 (d, J=15.0), 5.78-5.84 (m), $^{13}$C NMR (CD₃OD, 125 MHz) 21.1, 21.5, 29.3, 30.6, 36.4, 36.5, 40.2, 40.5, 44.1, 70.5, 77.4, 116.3, 137.6, 174.0, 176.1, 199.9, LR-APCIMS m/z 360.90 [M+H]⁺, 721.25 [2M+H]⁺, C₁₆H₂₈N₂O₅S.

S5 (10-undecenoyl-D-pantetheine): $^1$H NMR (CD₃OD, 500 MHz) 0.92 (s), 1.38 (t), 1.64 (m), 2.04 (q), 2.41 (t), 2.58 (t), 3.00 (t), 3.32-3.50 (m), 3.90 (s), 4.90-4.92 (dd), 4.96-5.00 (m), 5.77-5.81 (m) $^{13}$C NMR (CD₃OD, 125 MHz) 21.1, 21.4, 26.8, 29.2, 30.1, 30.2, 30.2, 30.4, 30.5, 35.0, 36.4, 36.5, 40.2, 40.5, 44.9, 70.5, 77.3, 114.9, 140.2, 173.9, 176.1, 200.7, LR-APCIMS m/z 443.10 [M−H]⁻, 415.10 [M+H]⁺, $C_{22}H_{40}N_2O_5S$.

S6 (isobutyl formate-D-pantetheine): ¹H NMR (CD₃OD, 500 MHz) 0.92 (s), 0.94 (d, J=10.0), 1.95 (m), 2.42 (t), 2.98 (t), 3.38-3.50 (m), 3.89 (s), 4.01 (d, J=5.0), ¹³C NMR (CD₃OD, 125 MHz) 19.3, 21.0, 21.5, 29.2, 31.3, 36.4, 36.5, 40.4, 40.5, 70.5, 74.6, 77.3, 172.1, 174.0, 176.1, LR-APCIMS m/z 376.95 [M−H]⁻, 378.90 [M+H]⁺, $C_{16}H_{30}N_2O_6S$.

S7 (2,4-dihydroxybenzoyl-D-pantetheine): ¹H NMR (CD₃OD, 500 MHz) 0.91 (s), 2.43 (t), 2.72 (t), 3.35-3.51 (m), 3.85 (s), 3.89 (s), 6.27 (d, J=2.5), 6.36 (dd, J=2.0, 10.0), 7.72 (d, J=10.0), ¹³C NMR (CD₃OD, 125 MHz) 21.0, 21.5, 32.8, 36.5, 36.6, 37.3, 39.6, 40.5, 70.5, 77.4, 103.9, 109.5, 112.7, 134.5, 166.9, 167.1, 174.0, 176.2, 201.0, LR-APCIMS m/z 427.13 [M−H]⁻, 429.13 [M+H]⁺, $C_{19}H_{28}N_2O_7S$.

S8 (geranyl-D-pantetheine): ¹H NMR (CD₃OD, 500 MHz) 0.92 (s), 1.61 (s), 1.67 (s), 1.68 (s), 2.05 (t), 2.12 (q), 2.42 (t), 2.57 (t), 3.18 (d, J=8.0), 3.34-3.53 (m), 3.89 (s), 5.10 (t), 5.23 (t)¹³C NMR (CD₃OD, 125 MHz) 16.3, 17.9, 21.1, 21.5, 26.1, 27.7, 29.9, 31.3, 36.5, 36.6, 40.2, 40.5, 40.8, 70.5, 77.4, 122.1, 125.3, 132.6, 140.1, 173.9, 176.2, LR-APCIMS m/z 413.09 [M−H]⁻, 414.84 [M+H]⁺, $C_{22}H_{40}N_2O_5S$.

5. Effects of New D-Pantetheine Compounds on Hair Loss Prevention/Hair Growth Promotion Dermal papilla cells play a key role in the production and growth of hair, and compounds that promote the growth of dermal papilla cells are attracting attention as agents for preventing hair loss and promoting hair growth. In the present invention, in order to develop novel compounds for hair loss prevention and hair growth promotion, the effects of the new natural compounds and derivatives thereof on the promotion of growth of dermal papilla cells were measured.

(1) Measurement of Viability of Dermal Papilla Cells

For cell culture, Dulbecco's Modified Eagle Medium (DMEM), fetal bovine serum (FBS), 0.25% trypsin-1 mM EDTA, and penicillin-streptomycin were used, and dermal papilla cells were cultured at 37° C. in a humidified 5% $CO_2$. The medium was replaced twice a week, and the cultured dermal papilla cells were washed with PBS within 6-7 days. Next, the attached cells were separated by 0.05% trypsin-0.02% EDTA, centrifuged, and then subcultured for experiments. Specifically, 200 µl of dermal papilla cells were dispensed into each well of a 96-well plate at a density of $1 \times 10^4$ cells/well, and cultured under the conditions of 37° C. and 5% $CO_2$ for 18 hours so as to be attached to each well. After 18 hours, the medium was removed, and 200 µl of samples was added to each well having the cells attached thereto, followed by culture for 24 hours. After the medium was removed, 100 µl of a solution of 3-(4,5-dimethylthiazol)-2,5-diphenyltetrazoliumbromide(MTT), prepared by dissolving MTT in PBS at a concentration of 500 µg/ml, was added to the cultured cells, followed by culture for 4 hours under the same conditions as described above. The formed formazan crystal was dissolved in DMSO, and the absorbance at 570 nm was measured using an ELISA reader. The measured OD values ranging from 0.00 to 3.50 were used for the experimental results. The sample for treatment of the cells was used at concentrations of 0.5, 5 and 50 µM.

(2) Effects on Promotion of Growth of Dermal Papilla Cells

Figure 3:
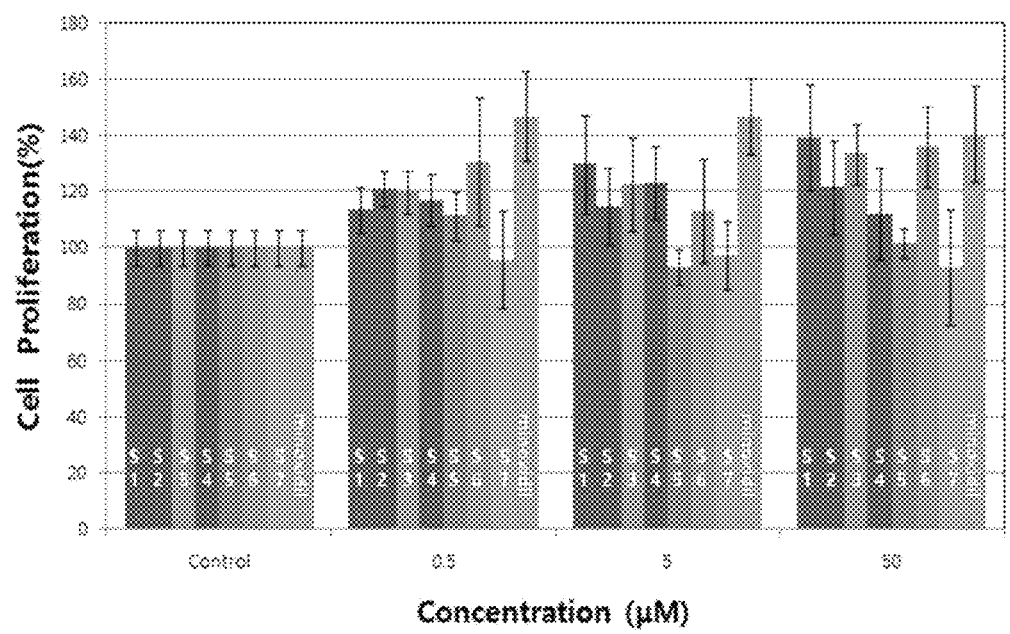
FIG. 3 shows the effects of new D-pantetheine derivatives according to the present invention on the promotion of proliferation of dermal papilla cells.

The results of the experiment for the new pantetheine compounds obtained in the present invention (see FIG. 3 and Table 3) indicated that the pantetheine compounds showed excellent effects on the promotion of growth of dermal papilla cells, and particularly, in the case of S1 and S6 among these compounds, the dermal papilla cell proliferation rate increased up to 140%.

Although the effects of all the compounds represented by formula 1 according to the present invention on the promotion of growth of dermal papilla cells were not examined, it will be obvious that the compounds that were not examined show effects equal to those of compounds S1-S7, because these compounds have the same backbone structure as that of compounds S1-S7 and differ from compounds S1-S7 only in terms of the substituent groups.

TABLE 3

| Effect of compounds S1-S7 on the growth of dermal papilla cells | | | | |
|---|---|---|---|---|
| Concentration (µM) | Control | 0.5 | 5 | 50 |
| S1 (2-methylbutyryl-pantetheine) | 100 | 113.31 | 129.65 | 139.19 |
| S2 (3-methylbutyryl-pantetheine) | 100 | 121.04 | 114.65 | 121.28 |
| S3 (cinnamoyl-pantetheine) | 100 | 119.77 | 122.38 | 133.33 |
| S4 (4-pentenoyl-pantetheine) | 100 | 116.88 | 122.89 | 111.97 |
| S5 (10-undecenoyl-pantetheine) | 100 | 111.24 | 93.01 | 101.62 |
| S6 (isobutyl formate-pantetheine) | 100 | 130.57 | 112.94 | 135.95 |
| S7 (2,4-dihydroxybenzoyl-pantetheine) | 100 | 95.73 | 97.32 | 93.12 |
| minoxidil | 100 | 146.66 | 146.52 | 140.29 |

As described above, the compounds according to the present invention showed activities of promoting the growth of dermal papilla cells, at levels almost equal to that of minoxidil, and are new compounds that have not yet been reported. These compounds of the present invention have a low molecular weight and are also easily synthesized. Thus, the possibility for these compounds to be developed into cosmetic or medical products for hair loss prevention and hair growth promotion is very high.

Although the specific embodiments of the present invention have been disclosed for illustrative purposes, those skilled in the art will appreciate that various modifications, additions and substitutions are possible without departing from the scope and spirit of the invention as disclosed in the accompanying claims.

What is claimed is:

1. A composition for promoting hair growth, containing, as an active ingredient, a compound represented by the following formula 1 or a salt thereof:

Formula 1

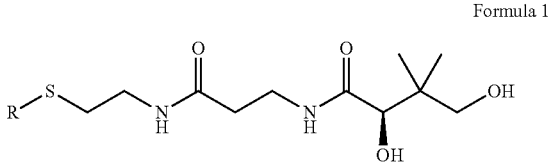

wherein R is any one selected from the group consisting of 4-pentenoyl, 10-undecenoyl, isobutyl formate, and 2,4-dihydroxybenzoyl.

2. The composition of claim 1, wherein the compound represented by formula 1 is any one selected from the group consisting of 4-pentenoyl-D-pantetheine, 10-undecenoyl-D-pantetheine, isobutyl formate-D-pantetheine, and 2,4-dihydroxybenzoyl-D-pantetheine.

3. The composition of claim 1, wherein the compound represented by formula 1 exhibits an effect of promoting growth of dermal papilla cells.

4. The composition of claim 1, wherein the compound represented by formula 1 is prepared using D-pantethine as a starting material.

5. The composition of claim 1, wherein the composition is a cosmetic composition for preventing hair loss and promoting hair growth.

6. The composition of claim 5, wherein the cosmetic composition has any one formation selected from the group consisting of hair tonics, hair conditioners, hair essence, hair lotion, hair nourishing lotion, hair shampoo, hair rinse, hair treatments, hair cream, hair nourishing cream, hair moisturizer cream, hair massage cream, hair wax, hair aerosols, hair packs, hair nourishing pack, hair soap, hair cleansing foam, hair oil, hair drying preparations, hair preservation treatments, hair colorants, hair weaving preparations, color-removing preparations for hair, hair gel, hair glazes, hair dressingers, hair lacquers, hair moisturizers, hair mousse, and hair sprays.

7. The composition of claim 1, wherein the composition is a pharmaceutical composition for preventing hair loss and promoting hair growth.

8. The composition of claim 7, wherein the pharmaceutical composition has any one formation selected from the group consisting of ointments, pastes, gels, jellies, serums, aerosol sprays, non-aerosol sprays, foams, creams, lotions, solutions, and suspensions.

* * * * *